(12) United States Patent
Chouzier et al.

(10) Patent No.: US 8,853,461 B2
(45) Date of Patent: Oct. 7, 2014

(54) METHOD FOR PREPARING A DEPEROXIDATION CATALYST

(75) Inventors: Sandra Chouzier, Lyons (FR); Serge Veracini, Lyons (FR); Françoise Igersheim, Lyons (FR)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 13/510,988

(22) PCT Filed: Nov. 18, 2010

(86) PCT No.: PCT/EP2010/067752
§ 371 (c)(1),
(2), (4) Date: Aug. 10, 2012

(87) PCT Pub. No.: WO2011/064135
PCT Pub. Date: Jun. 3, 2011

(65) Prior Publication Data
US 2012/0310012 A1    Dec. 6, 2012

(30) Foreign Application Priority Data
Nov. 30, 2009 (FR) ...................................... 09 58500

(51) Int. Cl.
*C07C 45/53* (2006.01)
*C07C 29/132* (2006.01)
*B01J 31/02* (2006.01)

(52) U.S. Cl.
CPC ......... *B01J 31/0212* (2013.01); *C07C 2101/14* (2013.01); *C07C 45/53* (2013.01); *C07C 29/132* (2013.01)
USPC ........... 568/342; 568/708; 568/821; 502/162; 502/171

(58) Field of Classification Search
USPC .................. 568/342, 700, 821; 502/162, 171
See application file for complete search history.

(56) References Cited

U.S. PATENT DOCUMENTS

| | | | |
|---|---|---|---|
| 2,169,368 A | 8/1939 | Murray et al. |
| 3,479,394 A | 11/1969 | Brunie et al. |
| 3,923,895 A | 12/1975 | Costantini |
| 4,371,471 A | 2/1983 | de Soyres et al. |
| 4,877,903 A | 10/1989 | Costantini et al. |
| 5,496,806 A | 3/1996 | Klemke |

FOREIGN PATENT DOCUMENTS

| | | |
|---|---|---|
| EP | 0023464 A1 | 2/1981 |
| GB | 777087 | 6/1957 |
| GB | 964869 | 7/1964 |
| GB | 1112837 | 5/1968 |
| GB | 1191573 | 5/1970 |
| GB | 1229734 | 4/1971 |

OTHER PUBLICATIONS

International Search Report issued by the European Patent Office in corresponding International Patent Application No. PCT/EP2010/067752 on Feb. 14, 2011, and an English language translation of the International Search Report.

*Primary Examiner* — Sikarl Witherspoon
(74) *Attorney, Agent, or Firm* — Dentons US LLP

(57) ABSTRACT

A process for preparing a deperoxidation catalyst comprising chromium as the main catalytic element is described. Also described, is a process for preparing an organic solution of a chromic acid ester. The solution can be used as a catalyst in a deperoxidation of an alkyl peroxide in a process for manufacturing cyclohexanol/cyclohexanone by oxidation of cyclohexane.

13 Claims, No Drawings

METHOD FOR PREPARING A DEPEROXIDATION CATALYST

CROSS-REFERENCE TO PRIOR APPLICATIONS

This application is a National Stage of PCT/EP2010/067752, filed Nov. 18, 2010, and designating the United States (published in the French language on Jun. 3, 2011, as WO 2011/064135 A1; the title and abstract were also published in English), which claims priority of FR 0958500, filed Nov. 30, 2009, each hereby expressly incorporated by reference in its entirety and each assigned to the assignee hereof.

The present invention relates to a process for preparing a deperoxidation catalyst comprising chromium as the main catalytic element.

It relates more particularly to a process for preparing an organic solution of a chromic acid ester, this solution being used as a catalyst in the step of deperoxidation of an alkyl peroxide, especially in the step of deperoxidation of cyclohexyl hydroperoxide, in the process for manufacturing cyclohexanol/cyclohexanone by oxidation of cyclohexane. The cyclohexanol and/or cyclohexanone are, in particular, intermediate products used in the manufacture of adipic acid or of epsilon-caprolactam, which are monomers for the production de polyamides.

Certain processes for the synthesis of oxidized compounds such as acids, diacids, alcohols and ketones, use peroxidized compounds as raw materials or as intermediate compounds. These compounds must be deperoxidized or decomposed in a specific step in order to obtain one or more oxidized products such as alcohols, ketones, acids or aldehydes.

One of the major industrial processes belonging to this group is the process for manufacturing diacids, more particularly adipic acid, by oxidation of cyclohexane to cyclohexyl hydroperoxide then decomposition, by deperoxidation, of this peroxide to alcohol and/or ketone. The latter oxidized compounds are then converted to diacids, mainly adipic acid, via oxidation by nitric acid.

The oxidation of cyclohexane to cyclohexyl hydroperoxide is carried out in a liquid medium by an oxygen-containing gas and in the absence of catalyst. This step is described, in particular, in patents GB 777087, GB 1112837, GB 964869, GB 1191573, U.S. Pat. No. 3,479,394 and U.S. Pat. No. 4,877,903.

After optionally removing the unreacted cyclohexane and washing the reaction medium with water in order to recover and extract certain by-products formed, the cyclohexyl hydroperoxide is decomposed by deperoxidation to cyclohexanone and cyclohexanol, in the presence of a catalyst comprising, as the main catalytic element, chromium, preferably in the form of chromium compounds of 6+ valency such as, for example, a chromic acid ester. This step is described, in particular, in French patent 1580206.

Generally, the catalyst used is in solution in an organic medium in order to be present in the reaction medium in dissolved form. Thus, di-tert-butyl chromate is the preferred chromium compound for the decomposition of cyclohexyl hydroperoxide.

Such a product is known and can be synthesized via various methods.

However, no manufacturing process described makes it possible to manufacture such a catalyst productively, in a form suitable for being introduced into a process for decomposition of an alkyl hydroperoxide and without producing chromium-containing effluents, which are harmful to the environment.

For this purpose, the invention proposes a process for preparing a catalyst for the deperoxidation of an alkyl hydroperoxide comprising chromium in the 6+ oxidation state as the main catalytic element. This process comprises the following steps:

dissolving chromic anhydride in water,
adding to the aqueous solution of chromic anhydride, a tertiary alcohol comprising at least 4 carbon atoms and a hydrocarbon solvent,
reacting the alcohol and the chromic anhydride, in order to obtain an alkyl chromate, by putting the reaction medium under reduced pressure at a temperature between 20 and 40° C., and distilling the water contained in the reaction medium,
recovering the catalyst in the form of a chromic acid ester in solution in the hydrocarbon.

According to one preferred embodiment of the invention, the concentration of chromic anhydride in the aqueous solution is between 35 and 75% by weight, preferably between 45 and 70% by weight and more preferably still between 55 and 65% by weight.

Putting the chromic acid into aqueous solution is advantageous for safety reasons. This is because the direct use of the chromic anhydride in an organic solution comprising a tertiary alcohol and a hydrocarbon solvent is not easily controllable on an industrial scale and runs the risk of generating an unstable mixture, especially in the event of an interruption in the supply of the alcohol.

According to one feature of the invention, the water is removed from the reaction medium by distillation in the form of an azeotrope formed in particular with the hydrocarbon solvent and/or optionally the alcohol. The removal of the water at this stage of the process makes it possible to avoid the formation of solid deposits during storage of the chromic ester solution.

According to another preferred feature of the invention, the chemical reaction of the alcohol and the chromic anhydride in aqueous solution and the removal of the water (water formed during the reaction and water used to dissolve the chromic anhydride) are carried out at the same time, in continuous mode in one and the same apparatus, advantageously a reactive distillation column. Thus, the aqueous solution of chromic anhydride is fed into the upper part of the column, the alcohol and the hydrocarbon being introduced at the top of the column. The solution of alkyl chromate is drawn off as a fraction from the bottom of the column. The alcohol and/or the hydrocarbon distilled together with the water is separated, for example, by decantation and recycled into the column. Besides the advantage of separating any heterogeneous aqueous phase from the chromic ester solution, thus preventing the formation of precipitates of chromium compounds, the continuous removal of water from the reaction medium by distillation under reduced pressure enables a quantitative esterification of the chromic anhydride used, and therefore a cleaner and more productive process.

The hydrocarbon solvents suitable for the invention are linear or cyclic saturated hydrocarbons such as cyclohexane, cyclooctane, cyclododecane, decalin or the like.

Preferably, the hydrocarbon solvent is the hydrocarbon corresponding to the one from which the peroxide to be decomposed is derived. Thus, in the process for manufacturing cyclohexanol and/or cyclohexanone, the compound to be deperoxidized is the cyclohexyl hydroperoxide obtained via oxidation of cyclohexane by oxygen. The solvent used is advantageously cyclohexane.

As alkyl hydroperoxides that are suitable for the invention, mention may be made of the hydroperoxides obtained via oxidation, by oxygen, of cyclic saturated hydrocarbons such as cyclohexane, cyclooctane, cyclododecane or decalin.

According to another preferred feature of the invention, the alcohols that are suitable for the invention are branched or unbranched, aliphatic tertiary saturated alcohols comprising at least 4 carbon atoms. The alcohol tert-butanol is the preferred alcohol.

The process of the invention allows a practically stoichiometric conversion of the chromic anhydride to alkyl chromate. This is because the reaction is performed under pressure conditions between 0.10 bar and 0.30 bar absolute and temperature conditions that make it possible to remove the water contained in the reaction medium and thus to shift the equilibrium of the esterification reaction. Furthermore, the temperature range between 20 and 40° C., preferably between 25 and 35° C., prevents the precipitation of the chromium in oxidized form.

The concentration of chromium in the reaction medium and the amount of hydrocarbon solvent added are determined in order to obtain a solution of chromic ester, preferably of di-tert-butyl chromate, which is stable and comprises between 2.5% by weight and 8% by weight of chromium, preferably between 3% by weight and 5% by weight, expressed as elemental chromium.

Advantageously, the chromic ester solution is stabilized by addition of a stabilizer chosen from esters of phosphoric acid, preferably octylphosphoric acid or isobutylphosphoric acid. The addition of the stabilizer may be carried out by adding it to the solution obtained or by feeding stabilizer, especially octylphosphoric acid, into the reactive column, for distillation of the water, described previously. Particularly advantageously, the stabilizer is added in an amount such that the phosphorus/chromium (P/Cr) molar ratio is less than 0.05, preferably between 0.02 and 0.05. Respecting this P/Cr molar ratio during the addition of the stabilizer makes it possible to prevent the precipitation of chromium oxide during the storage of the chromic ester solutions, without deactivating the catalyst.

The manufacturing process of the invention makes it possible to obtain a stable chromic ester solution with a very good productivity and a high yield obtained in particular by the continuous removal of the water. Furthermore, this process produces an effluent, distilled water, which is free of chromium.

The solution thus obtained can be used directly as a catalyst in a deperoxidation process, without risk of precipitation of chromium since it does not, in particular, contain water.

More particularly, this solution of alkyl chromate, preferably of di-tert-butyl chromate, is used as a catalyst in the step of deperoxidation of cyclohexyl hydroperoxide in order to produce a mixture of cyclohexanol/cyclohexanone by oxidation of cyclohexane. This mixture is oxidized with nitric acid in order to synthesize adipic acid.

Specifically, in this process, the cyclohexane in the liquid state is subjected to an oxidation by oxygen or an oxygen-containing gas in order to form cyclohexyl hydroperoxide and various other oxidized products. After separation of a portion of the cyclohexane that has not reacted and optionally extraction by water of oxidized compounds such as acidic primary aliphatic hydroperoxides, hydroxy acids and diacids, the cyclohexyl hydroperoxide in solution in cyclohexane is introduced into a deperoxidation step in order to be converted to cyclohexanone and/or cyclohexanol. This deperoxidation step is carried out in the presence of a catalyst based on chromium in the 6+ oxidation state.

According to one of the subjects of the invention, the catalyst supplied to this deperoxidation step is a solution of alkyl chromate, preferably of di-tert-butyl chromate, obtained according to a production process that conforms to the present invention.

The use of an organic catalyst solution prepared according to the process of the invention makes it possible to control the concentration of active catalyst (concentration of chromium in the 6+ oxidation state) in the reaction medium, and consequently the degree of conversion or decomposition of the cyclohexyl hydroperoxide. The catalyst remains in dissolved form in the reaction medium up to a very high degree of conversion of the cyclohexyl hydroperoxide (degree of conversion greater than 90%). In the case of a use of a catalyst solution that contains water, a precipitate of chromium oxide appears, which is a significant drawback for carrying out the process and for the economics thereof.

Other advantages and details of the invention will appear in light of the examples given below solely by way of illustration, with no limiting character.

EXAMPLE 1

Preparation of a Solution of Di-tert-butyl Chromate According to the Invention

Chromic anhydride $CrO_3$ is dissolved in water to obtain a solution of chromic acid having a concentration of 60% by weight.

This aqueous solution of chromic acid is fed, with a flow rate of 13 kg/h, into a ten-plate distillation column, level with a plate located in the vicinity of the top of the column.

The tert-butanol alcohol and the hydrocarbon solvent (cyclohexane) are fed into the top of the column with respective flow rates of 16 and 90 kg/h.

Octylphosphoric acid is added as a stabilizer at the top of the column with a flow rate of 1 kg/h.

As indicated previously, this compound may be added to the chromic ester solution recovered at the bottom of the column.

The column operates under a pressure of 130 mmHg (0.17 bar) with a temperature at the bottom of the column of 30° C.

At the top of the distillation column, a fraction containing the water/tert-butanol/cyclohexane azeotrope is recovered. After decantation, the organic phase containing the cyclohexane and alcohol is recycled into the column, the aqueous phase, which is free of chromium, being removed.

At the bottom of the distillation column, the solution of di-tert-butyl chromate is recovered.

The solution thus prepared is fed into the reactor for decomposition of cyclohexyl hydroperoxide.

EXAMPLE 2

Preparation of a Solution of Di-tert-butyl Chromate According to the Invention

Chromic anhydride $CrO_3$ is dissolved in water to obtain a solution of chromic acid having a concentration of 60% by weight.

This aqueous solution of chromic acid is fed, with a flow rate of 15 kg/h, into a ten-plate distillation column, level with a plate located in the vicinity of the top of the column.

The tert-butanol alcohol and the hydrocarbon solvent (cyclohexane) are fed into the top of the column with respective flow rates of 21 and 125 kg/h.

Octylphosphoric acid is added as a stabilizer at the top of the column with a flow rate of 1.3 kg/h.

The column operates under a pressure of 120 mmHg (0.16 bar) with a temperature at the bottom of the column of 29.5° C.

At the top of the distillation column, a fraction containing the water/tert-butanol/cyclohexane azeotrope is recovered. After decantation, the organic phase containing the cyclohexane and alcohol is recycled into the column, the aqueous phase, which is free of chromium, being removed.

At the bottom of the distillation column, the solution of di-tert-butyl chromate is recovered.

The solution thus prepared is fed into the reactor for decomposition of cyclohexyl hydroperoxide.

EXAMPLE 3

Preparation of a Solution of Di-tert-butyl Chromate According to the Invention

Example 2 above is reproduced, except that isobutylphosphoric acid (instead of octylphosphoric acid) is added as stabilizer at the top of the column with a flow rate of 0.75 kg/h.

The column operates under the same conditions as those described in Example 2.

At the top of the distillation column, a fraction containing the water/tert-butanol/cyclohexane azeotrope is recovered. After decantation, the organic phase containing the cyclohexane and alcohol is recycled into the column, the aqueous phase, which is free of chromium, being removed.

At the bottom of the distillation column, the solution of di-tert-butyl chromate is recovered.

The solution thus prepared is fed into the reactor for decomposition of cyclohexyl hydroperoxide.

COMPARATIVE EXAMPLE

Preparation of a Solution of Di-tert-butyl Chromate without Continuous Removal of Water Chromic anhydride $CrO_3$ is dissolved in water to obtain a solution of chromic acid having a concentration of 70% by weight.

This aqueous solution of chromic acid is fed, with stirring at 20° C. (over 1 hour), with a flow rate of 85 kg/h, into a batch reactor comprising 78 kg of tert-butanol and 583 kg of cyclohexane.

After the end of the addition, the mixture continues to be stirred for a further 1 hour, then is left to settle for separation of the aqueous layer.

The amount of chromium present in the aqueous layer is assayed. The aqueous layer contains 17% (by weight) of the chromium supplied.

The invention claimed is:

1. A process for preparing a catalyst for the deperoxidation of an alkyl hydroperoxide, the process comprising:
dissolving chromic anhydride in water to form an aqueous solution,
adding to the aqueous solution of chromic anhydride, a tertiary alcohol comprising at least 4 carbon atoms and a hydrocarbon solvent,
reacting the alcohol and the chromic anhydride under reduced pressure in order to distill the water, at a temperature varying from 20° C. to 40° C., and
recovering the catalyst in the form of a chromic acid ester in solution in the hydrocarbon solvent, wherein the catalyst comprises chromium in the 6+ oxidation state as a main catalytic element.

2. The process according to claim 1, wherein the water is removed in the form of an azeotrope formed with the hydrocarbon solvent and/or the alcohol.

3. The process according to claim 1, wherein the reaction of the alcohol with the chromic anhydride in aqueous solution and the removal of the water are carried out at the same time, in continuous mode in one and the same apparatus.

4. The process according to claim 3, wherein the apparatus is a reactive distillation column, the aqueous solution of chromic anhydride being fed into an upper part of said column, the alcohol and the hydrocarbon being fed into a top of the column, and the solution of the chromic acid ester being drawn off as a fraction from a bottom of the column.

5. The process according to claim 1, wherein the hydrocarbon solvent is a saturated hydrocarbon.

6. The process according to claim 5, wherein the hydrocarbon is selected from the group consisting of cyclohexane, cyclooctane, cyclododecane and decalin.

7. The process according to claim 1, wherein the alcohol is tert-butanol.

8. The process according to claim 1, wherein the pressure at which the esterification step is carried out ranges from 0.10 bar to 0.30 bar absolute.

9. The process according to claim 1, wherein the organic chromic ester solution comprises from 2.5% to 8% by weight of chromium expressed as weight of elemental chromium.

10. The process according to claim 1, wherein the organic chromic ester solution is stabilized by addition of a stabilizer selected from the group consisting of an ester of phosphoric acid.

11. The process according to claim 10, wherein the stabilizer is added in an amount that results in a phosphorus/chromium (P/Cr) molar ratio that is less than 0.05.

12. The process according to claim 10, wherein the stabilizer is fed into the top of a reactive distillation column.

13. The process according to claim 10, wherein the stabilizer is octylphosphoric acid or isobitylphosphoric acid.

* * * * *